United States Patent [19]

Ohsawa et al.

[11] Patent Number: 5,739,377

[45] Date of Patent: Apr. 14, 1998

[54] PHENYLALKANOIC ACID ESTERS AND THEIR USE AS ANTIOXIDANTS

[75] Inventors: Hisayu Ohsawa; Tomoyuki Kurumada; Takaaki Yamazaki; Satoru Naito, all of Tokyo; Kohtaro Kanetaki, Kawasaki, all of Japan

[73] Assignee: Sankyo Company, Limited, Tokyo, Japan

[21] Appl. No.: 418,883

[22] Filed: Apr. 7, 1995

Related U.S. Application Data

[63] Continuation of Ser. No. 183,120, Jan. 18, 1994, abandoned.

[30] Foreign Application Priority Data

Jan. 21, 1993 [JP] Japan ......................... 5-008437

[51] Int. Cl.⁶ .................................................. C07C 69/76
[52] U.S. Cl. .................................................. 560/75
[58] Field of Search .................................................. 560/75

[56] References Cited

U.S. PATENT DOCUMENTS

| 4,032,562 | 6/1977 | Dexter, et al. ............... 560/55 |
| 5,206,414 | 4/1993 | Evans ........................... 560/75 |
| 5,427,591 | 6/1995 | Cherpeck . | |

FOREIGN PATENT DOCUMENTS

| 2133374 | 1/1972 | Germany . |
| A-36 39 354 | 1/1988 | Germany . |
| 2133374 | 1/1972 | Japan . |
| WO94/14748 | 7/1994 | WIPO . |

OTHER PUBLICATIONS

Derwent Abstract for WO 94/14748, Jul. 7, 1994.
Derwent Abstract for WO 94/14926, Jul. 7, 1994.
Chem Abstracts 78:112082 1973.

*Primary Examiner*—Paul J. Killos
*Attorney, Agent, or Firm*—Frishauf, Holtz, Goodman, Langer & Chick, P.C.

[57] ABSTRACT

Compounds of formula (I):

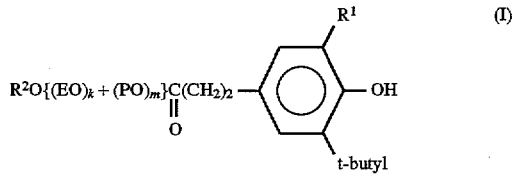

wherein:

$R^1$ represents an alkyl group having from 1 to 6 carbon atoms;

$R^2$ represents an alkyl group having from 8 to 24 carbon atoms;

EO represents an ethyleneoxy group;

PO represents a propyleneoxy group;

k is 0 or an integer from 1 to 10; and m is an integer from 1 to 4;

provided that the total of (k+m) is greater than 1 and not greater than 10;

are useful as antioxidant stabilizers for polymeric materials.

40 Claims, No Drawings

PHENYLALKANOIC ACID ESTERS AND THEIR USE AS ANTIOXIDANTS

This application is a Continuation of application Ser. No. 08/183,120, filed Jan. 18, 1994, now abandoned.

BACKGROUND TO THE INVENTION

The present invention relates to novel alkoxyalkylene glycol esters of substituted phenylpropionic acids and to their use as antioxidant stabilizers for organic materials subject to oxidative deterioration, such as synthetic polymers and resins.

It is generally necessary to incorporate antioxidants into materials made from organic polymers and resins, in order to arrest the effects of oxidative deterioration. Various hindered phenolic esters are known to be useful for this purpose, including some alkylene glycol esters of substituted phenylalkanoic acids. For example, British Patent No. 1,376,482 discloses 3,5-dialkyl-4-hydroxyphenylalkanoic acid esters with mono- or polyalkylene glycol alkyl monoethers and their use as antioxidants. However, the alkyl ether moiety in these compounds contains only 1 or 2 carbon atoms.

Most previously known antioxidants of this type are solids with relatively high melting points, which causes several problems in polymer processing plants. Such antioxidants are used in small quantities, and it is difficult to ensure their homogeneous distribution throughout a bulk polymeric material, with which they may have poor compatibility. Such miscibility problems are particularly great when adding a solid antioxidant to a liquid polymeric material, such as liquid polyols for polyurethanes or paints, and a readily miscible liquid stabilizer is desirable for this. Stabilizers which are liquids or low melting point solids are also much better suited for use with automatic metering equipment in modern synthetic resin manufacturing plants.

A further problem with solid stablizers arises in modern polyolefin manufacturing plants, where it is preferred to do away with melt mixing of the bulk polymer and stabilizer, and instead to treat large diameter polymer particles with stabilizer in the liquid phase, followed by drying.

Accordingly, there is a need for effective new antioxidants, which are liquids or low melting point solids, and consequently do not suffer from such problems.

BRIEF SUMMARY OF THE INVENTION

It is an object of the present invention to provide new substituted phenylpropionic acid esters of polyalkylene glycols which are effective as antioxidants for polymeric organic materials. It is another object of the invention to provide such esters which are liquids or low melting point solids, and which have good polymer compatibility, so that they may be readily incorporated into bulk polymeric materials. It is a further object of the invention to provide such novel esters with superior activity as antioxidant stabilizers for polymeric materials.

We have now surprisingly found that certain substituted phenylpropionic acid esters of mono- or polyalkylene glycol alkyl monoethers, wherein the alkyl ether moiety has 8 or more carbon atoms, overcome the above-described problems. These esters are liquids or low melting point solids, which exhibit good polymer compatibility, and also excellent antioxidant activity, heat stabilization and resistance to nitrogen oxides, in conjunction with low volatility and a reduced tendency to surface migration.

Thus, in a first aspect, the invention provides a compound of formula (I):

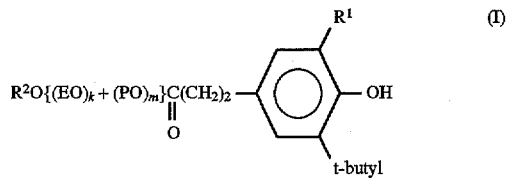

wherein:

$R^1$ represents an alkyl group having from 1 to 6 carbon atoms;

$R^2$ represents an alkyl group having from 8 to 24 carbon atoms;

EO represents an ethyleneoxy group;

PO represents a propyleneoxy group;

k is 0 or an integer from 1 to 10; and m is 0 or an integer from 1 to 5;

provided that the total of (k+m) is greater than 0 and not greater than 10.

The present invention further provides an antioxidant for organic polymeric materials, comprising at least one compound of the above formula (I) as an active ingredient.

DETAILED DESCRIPTION OF THE INVENTION

In the above formula (I), $R^1$ may be a straight or branched alkyl group having from 1 to 6 carbon atoms such as, for example, a methyl, ethyl, propyl, isopropyl, butyl, s-butyl, t-butyl, pentyl, isopentyl, t-pentyl, hexyl or isohexyl group. More preferably, $R^1$ represents an alkyl group having from 1 to 4 carbon atoms; and most preferably $R^1$ is a methyl or t-butyl group.

$R^2$ in the above formula (I) may be a straight or branched alkyl group having from 8 to 24 carbon atoms such as, for example, an octyl, 2-ethylhexyl, nonyl, decyl, undecyl, dodecyl, tridecyl, tetradecyl, pentadecyl, hexadecyl, heptadecyl, octadecyl, icosyl, henicosyl, docosyl, tricosyl or tetracosyl group. Preferably, $R^2$ represents a straight or branched alkyl group having from 8 to 18 carbon atoms, more preferably one with 12 to 18 carbon atoms, and most preferably one having from 16 to 18 carbon atoms.

The portion $\{(EO)_k + (PO)_m\}$ in formula (I) represents an ethylene oxide, polyethylene oxide, propylene oxide or polypropylene oxide group, or a mixed adduct formed from one or more ethylene oxide groups with one or more propylene oxide groups. In the case of such a mixed ethylene oxide/propylene oxide adduct, there is no restriction on the order of addition of the ethylene oxide and propylene oxide groups; and the indices k and m represent the average molar numbers for the ethylene oxide and propylene oxide units in the adduct.

The total of (k+m) in formula (I) is preferably from 1 to 8, more preferably from 1 to 6, and most preferably from 1 to 3.

A preferred sub-group of compounds within formula (I) are those wherein:

$R^1$ represents a straight or branched alkyl group having from 1 to 4 carbon atoms;

$R^2$ represents a straight or branched alkyl group having from 8 to 18 carbon atoms; and the total of (k+m) is from 1 to 8.

A more highly preferred sub-group of compounds within formula (I) are those wherein:

$R^1$ represents a methyl or t-butyl group;

$R^2$ represents a straight or branched alkyl group having from 12 to 18 carbon atoms; and the total of (k+m) is from 1 to 6.

The most highly preferred compounds of formula (I) are those wherein:

$R^1$ represents a t-butyl group;

$R^2$ represents a straight or branched alkyl group having from 16 to 18 carbon atoms; and the total of (k+m) is from 1 to 3.

Some typical examples of the compounds of formula (I) are shown in Table 1. The abbreviations used in this Table have the following meanings:

| Bu | butyl | Me | methyl |
|---|---|---|---|
| t-Bu | t-butyl | Oc | octyl |
| Dcs | docosyl | Ocdc | octadecyl |
| Ddc | dodecyl | PO | propyleneoxy |
| EO | ethyleneoxy | Pr | propyl |
| Et | ethyl | i-Pr | isopropyl |
| Hx | hexyl | Trdc | tridecyl |
| Hxdc | hexadecyl | Ttcs | tetracosyl |
| Ics | icosyl | | |

TABLE 1

| Compd. No. | $R^1$ | $[(EO)_k + (PO)_m]$ | $R^2$ |
|---|---|---|---|
| 1 | Me | $[(EO)_1]$ | 2-Et-Hx |
| 2 | Me | $[(EO)_2]$ | 2-Et-Hx |
| 3 | Et | $[(EO)_2]$ | 2-Et-Hx |
| 4 | Pr | $[(EO)_2]$ | 2-Et-Hx |
| 5 | t-Bu | $[(EO)_1]$ | 2-Et-Hx |
| 6 | t-Bu | $[(EO)_2]$ | 2-Et-Hx |
| 7 | t-Bu | $[(EO)_4]$ | 2-Et-Hx |
| 8 | t-Bu | $[(EO)_8]$ | 2-Et-Hx |
| 9 | t-Bu | $[(PO)_1]$ | 2-Et-Hx |
| 10 | t-Bu | $[(PO)_2]$ | 2-Et-Hx |
| 11 | t-Bu | $[(EO)_2 + (PO)_1]$ | 2-Et-Hx |
| 12 | t-Bu | $[(EO)_2 + (PO)_2]$ | 2-Et-Hx |
| 13 | Me | $[(EO)_1]$ | Oc |
| 14 | Me | $[(EO)_2]$ | Oc |
| 15 | t-Bu | $[(EO)_1]$ | Oc |
| 16 | t-Bu | $[(EO)_2]$ | Oc |
| 17 | t-Bu | $[(EO)_2]$ | 3,5,5-Me$_3$-Hx |
| 18 | Me | $[(EO)_1]$ | Ddc |
| 19 | Me | $[(EO)_2]$ | Ddc |
| 20 | t-Bu | $[(EO)_1]$ | Ddc |
| 21 | t-Bu | $[(EO)_2]$ | Ddc |
| 22 | t-Bu | $[(EO)_4]$ | Ddc |
| 23 | t-Bu | $[(EO)_8]$ | Ddc |
| 24 | t-Bu | $[(PO)_2]$ | Ddc |
| 25 | t-Bu | $[(EO)_2]$ | Trdc |
| 26 | t-Bu | $[(PO)_2]$ | Trdc |
| 27 | Me | $[(EO)_1]$ | Hxdc |
| 28 | Me | $[(EO)_2]$ | Hxdc |
| 29 | Me | $[(EO)_3]$ | Hxdc |
| 30 | Me | $[(EO)_4]$ | Hxdc |
| 31 | Me | $[(PO)_1]$ | Hxdc |
| 32 | Me | $[(EO)_2 + (PO)_1]$ | Hxdc |
| 33 | Et | $[(EO)_2]$ | Hxdc |
| 34 | i-Pr | $[(EO)_2]$ | Hxdc |
| 35 | t-Bu | $[(EO)_1]$ | Hxdc |
| 36 | t-Bu | $[(EO)_2]$ | Hxdc |
| 37 | t-Bu | $[(EO)_3]$ | Hxdc |
| 38 | t-Bu | $[(EO)_4]$ | Hxdc |
| 39 | t-Bu | $[(EO)_6]$ | Hxdc |
| 40 | t-Bu | $[(EO)_8]$ | Hxdc |
| 41 | t-Bu | $[(PO)_1]$ | Hxdc |
| 42 | t-Bu | $[(PO)_2]$ | Hxdc |
| 43 | t-Bu | $[(PO)_3]$ | Hxdc |
| 44 | t-Bu | $[(EO)_2 + (PO)_1]$ | Hxdc |
| 45 | t-Bu | $[(EO)_3 + (PO)_1]$ | Hxdc |
| 46 | t-Bu | $[(EO)_6 + (PO)_4]$ | Hxdc |

TABLE 1-continued

| Compd. No. | $R^1$ | $[(EO)_k + (PO)_m]$ | $R^2$ |
|---|---|---|---|
| 47 | Me | $[(EO)_1]$ | Ocdc |
| 48 | Me | $[(EO)_2]$ | Ocdc |
| 49 | Me | $[(EO)_4]$ | Ocdc |
| 50 | Me | $[(PO)_2]$ | Ocdc |
| 51 | Me | $[(EO)_2 + (PO)_1]$ | Ocdc |
| 52 | t-Bu | $[(EO)_1]$ | Ocdc |
| 53 | t-Bu | $[(EO)_2]$ | Ocdc |
| 54 | t-Bu | $[(PO)_3]$ | Ocdc |
| 55 | t-Bu | $[(PO)_7]$ | Ocdc |
| 56 | t-Bu | $[(EO)_8]$ | Ocdc |
| 57 | t-Bu | $[(EO)_{10}]$ | Ocdc |
| 58 | t-Bu | $[(PO)_2]$ | Ocdc |
| 59 | t-Bu | $[(PO)_3]$ | Ocdc |
| 60 | t-Bu | $[(EO)_2 + (PO)_1]$ | Ocdc |
| 61 | t-Bu | $[(EO)_{10} + (PO)_2]$ | Ocdc |
| 62 | t-Bu | $[(EO)_2 + (PO)_2]$ | Ocdc |
| 63 | t-Bu | $[(EO)_1]$ | Ics |
| 64 | t-Bu | $[(EO)_2]$ | Ics |
| 65 | t-Bu | $[(EO)_4]$ | Ics |
| 66 | t-Bu | $[(PO)_2]$ | Ics |
| 67 | t-Bu | $[(PO)_4]$ | Ics |
| 68 | t-Bu | $[(EO)_2 + (PO)_1]$ | Ics |
| 69 | t-Bu | $[(EO)_2]$ | Dcs |
| 70 | t-Bu | $[(PO)_2]$ | Ttcs |

Among the compounds listed in Table 1, the following are preferred, namely Compounds Nos. 7, 8, 11, 16, 18, 19, 20, 21, 22, 23, 24, 25, 26, 27, 28, 29, 31, 32, 35, 36, 37, 38, 39, 40, 41, 42, 43, 44, 45, 46, 47, 48, 49, 50, 51, 52, 53, 54, 55, 56, 57, 58, 59, 60, 62 and 64, of which Compounds Nos. 8, 11, 21, 22, 23, 24, 28, 35, 36, 37, 41, 42, 43, 52, 53, 54, 58 and 59 are more preferred.

The compounds of the present invention can be prepared by any suitable method generally known in the art for the preparation of compounds of this type, including various esterification methods. Three examples of such methods are illustrated in the following reaction schemes, respectively labelled Method A, Method B and Method C.

1) Method A

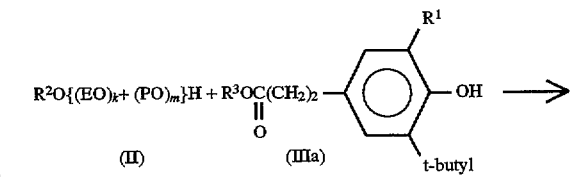

2) Method B

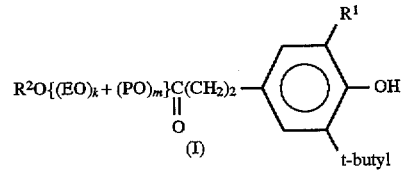

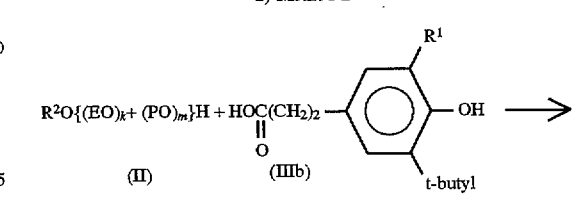

-continued

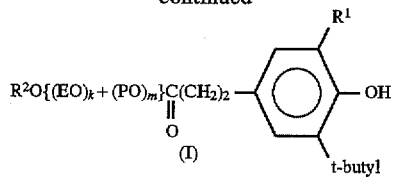

(I)

3) Method C

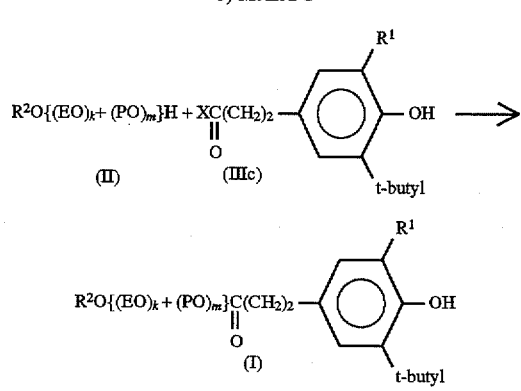

In the above reaction schemes:

$R^1$, $R^2$, k and m have the meanings previously defined for formula (I);

$R^3$ represents a straight or branched alkyl group having from 1 to 4 carbon atoms such as, for example, a methyl, ethyl, propyl, isopropyl, butyl or isobutyl group, and preferably represents a methyl group; and X represents a halogen atom such as chlorine or bromine.

The starting materials of formula (II) are adducts of alkylene oxides with various alcohols, which may be described as alkylene glycol alkyl monoethers or as O-alkylated alkylene glycols. It will be appreciated that, in the case of polyalkylene oxide adducts, the commercially available products are often mixtures of several individual compounds with varying numbers of ethylene oxide and/or propylene oxide units; and, if such a mixture is used as the starting material, the end product of formula (I) will be constituted of a corresponding mixture. Accordingly, it should be understood that, in such mixtures, the indices k and m may represent the average number of ethylene oxide and propylene oxide units, respectively, and may therefore be fractional numbers for the overall mixture.

Method A involves a transesterification between the alkylene glycol monoether of formula (II) and the substituted phenylpropionic acid ester of formula (IIIa). This reaction may be performed in the presence or absence of a solvent, as desired, and in the presence of a transesterification catalyst.

If a solvent is used for this reaction, suitable inert solvents include, for example, ethers such as diisopropyl ether, dioxane and tetrahydrofuran, halogenated hydrocarbons such as carbon tetrachloride and dichloroethane, linear or cyclic aliphatic hydrocarbons such as hexane, heptane, octane, isooctane, cyclohexane, methylcyclohexane, ethylcyclohexane and kerosine, and aromatic hydrocarbons such as benzene, toluene and xylene. Aromatic hydrocarbons are preferred.

Suitable transesterification catalysts include, for example, alkali metals such as lithium, sodium and potassium, alkali metal amides such as lithium amide, sodium amide, and lithium N,N,-diisopropylamide, alkali metal alkoxides such as sodium methoxide, sodium ethoxide and potassium t-butoxide, alkali metal hydroxides such as lithium hydroxide, sodium hydroxide and potassium hydroxide, alkali metal carbonates such as lithium carbonate, sodium carbonate and potassium carbonate, alkali metal bicarbonates such as lithium bicarbonate, sodium bicarbonate and potassium bicarbonate, titanium (IV) alkoxides such as titanium (IV) tetraisopropoxide and titanium (IV) tetrabutoxide, and metal oxide salts such as tin oxide. Alkali metal alkoxides are preferred.

The reaction temperature and time can vary, depending upon the starting materials, catalyst and solvent (if any) employed. However, a temperature from 50° C. to 200° C. will generally be used, more preferably from 80° C. to 140° C.; and the reaction time is usually from 2 to 24 hours, more preferably from 4 to 12 hours.

After completion of the transesterification reaction, the desired product of formula (I) can be isolated by means of conventional techniques. For example, the reaction mixture is washed and neutralised with a dilute mineral acid (e.g. dilute hydrochloric or sulfuric acid), insolubles are removed (e.g. by filtration), the resulting liquid is dried over a dehydrating agent (e.g. anhydrous magnesium sulfate), and the solvent is evaporated off. If desired, the resulting product can be purified, for example by distillation under reduced pressure or column chromatography.

Method B involves the esterification of the alkylene glycol monoether of formula (II) with the substituted phenylpropionic acid of formula (IIIb). This reaction is generally carried out in an inert solvent and in the presence of an acid catalyst.

Suitable inert solvents whicn may be used for this reaction include, for example, ethers such as diisopropyl ether, dioxane and tetrahydrofuran, halogenated hydrocarbons such as methylene chloride, carbon tetrachloride and dichloroethane, aliphatic hydrocarbons such as hexane, heptane, octane, ethylcyclohexane and kerosine, and aromatic hydrocarbons such as benzene, toluene and xylene. Aromatic hydrocarbons are preferred.

The acid catalysts which may be used for this reaction include, for example, sulfonic acids such as benzenesulfonic acid, p-toluenesulfonic acid, trifluoromethanesulfonic acid and methanesulfonic acid, and mineral acids such as hydrochloric acid and sulfuric acid, Mineral acids and sulfonic acids are preferred, more particularly sulfuric acid as the mineral acid and p-toluenesulfonic acid as the sulfonic acid.

The reaction temperature and time can vary, depending upon the starting materials, solvent and catalyst; but the temperature will generally be from 60° C. to 200° C., more preferably from 100° C. to 150° C., and the reaction time will generally be from 3 hours to 24 hours, more preferably from 4 hours to 12 hours.

After completion of the esterification reaction, the desired product of formula (I) can be isolated by conventional techniques. For example, the reaction mixture is washed and neutralised with an aqueous alkali solution (e.g. aqueous sodium bicarbonate), insolubles are removed (e.g. by filtration), the resulting liquid ms dried over a dehydrating agent (e.g. anhydrous magnesium sulfate), and the solvent is evaporated off to give the product of formula (I). If desired, the product can be purified, for example by distillation under reduced pressure or by column chromatography.

Method C involves the esterification of the alkylene glycol monoether of formula (II) with the substituted phenylpropionic acid halide of formula (IIIc). This reaction is generally carried out in an inert solvent, and in the presence of a hydrogen halide scavenger.

Examples of suitable solvents for this reaction include those already listed above for the reaction of Method A.

Examples of suitable hydrogen halide scavengers include alkali metal hydroxides such as lithium hydroxide, sodium hydroxide and potassium hydroxide, alkali metal carbonates such as lithium carbonate, sodium carbonate and potassium carbonate, alkali metal bicarbonates such as lithium bicarbonate, sodium bicarbonate and potassium bicarbonate, aliphatic tertiary amines such as triethylamine, trioctylamine, N-methylmorpholine and N,N-dimethylpiperazine, and pyridines such as pyridine and N,N-dimethylaminopyridine. Triethylamine and pyridines are preferred.

The reaction temperature and time can vary, depending upon the starting materials, solvent and hydrogen halide scavenger employed. However, the reaction temperature will usually be from 0° C. to 120° C., more preferably from 10° C. to 60° C., and the reaction time will usually be from 1 hour to 12 hours, more preferably from 4 hours to 8 hours.

After completion of the reaction, the desired product of formula (I) can be isolated by means of conventional techniques. For example, the reaction mixture is washed with a dilute mineral acid (e.g. dilute hydrochloric or sulfuric acid), insolubles are removed (e.g. by filtration), the resulting liquid is dried over a dehydrating agent (e.g. anhydrous magnesium sulfate), and the solvent is evaporated off to give the desired product. If desired, the product can be purified for example by distillation under reduced pressure or by column chromatography.

We have discovered that the compounds of formula (I) exhibit excellent polymer compatibility, heat stabilization and resistance to nitrogen oxides, in conjunction with low volatility and a reduced tendency to surface migration. This combination of properties renders them valuable as novel antioxidant stabilizers for organic materials such as fats, lubricants and polymeric materials.

The antioxidant compounds of the invention can be incorporated with the organic material to be stabilized by means of per se known techniques, at any suitable stage. For example, they can be added before or after polymerization, or during a processing step such as injection molding. For example, the antioxidant may be mixed with a granular or powdery polymeric material; or a solution or suspension of the antioxidant may be mixed with the polymeric material, and the mixture dried; or the antioxidant may be mixed with a liquid monomer, polyol, isocyanate, plasticizer or prepolymer, and the resulting pre-mix then mixed with the polymeric material. The antioxidants of the invention may also be used in conjunction with other additives which are conventionally used in the field of polymer technology.

Suitable synthetic resins and polymeric materials for use with the antioxidant stabilizers of the present invention include the following:

Olefins and diene polymers

Homopolymers of olefins and dienes (e.g. low density, linear low density, high density and cross-linked polyethylenes, polypropylene, polyisobutene, polymethylbutene-1, polymethylpentene-1, polyisoprene and polybutadiene); mixtures of such homopolymers (e.g. mixtures of polypropylene and polyethylene, of polypropylene and polybutene-1 and of polypropylene and polyisobutylene); copolymers of olefins (e.g. ethylene-propylene copolymer, propylene-butene-1 copolymer and ethylene-butene-1 copolymer); copolymers of olefins and dienes (e.g. terpolymers of ethylene, propylene and dienes, such as butadiene, hexadiene, dicyclopentadiene and ethylidene norbornene); and natural rubbers;

Styrene polymers

Polystyrene, poly-α-methylstyrene, and copolymers of styrene or α-methylstyrene (e.g. styrene-maleic anhydride copolymer, styrene-butadiene copolymer, styrene-acrylonitrile-methyl methacrylate copolymer, styrene-acrylonitrile-acrylate copolymer, styrene-acrylonitrile copolymer modified with an acrylate for impact strength, and styrene polymer modified with an ethylene propylene diene monomer, also for impact strength); and graft copolymers of styrene [e.g. a graft copolymer of styrene and polybutadiene, graft copolymers of styrene and acrylonitrile to polybutadiene (generally referred to as acrylonitrile-butadiene-styrene polymers), mixtures of such graft copolymers with the styrene copolymers given above] and heat-resistant acrylonitrile-butadiene-styrene polymers copolymerised with maleimide derivatives;

Vinyl halide, vinylidene halide and halogeneted olefin polymers

Polyvinyl chloride, polyvinylidene chloride, polyvinyl fluoride, polyvinylidene fluoride, polychloroprene, vinyl chloride-vinylidene chloride copolymer, vinyl chloride-vinyl acetate copolymer, vinyl chloride-ethylene copolymer, vinylidene chloride-vinyl acetate copolymer chlorinated polyethylene, chlorinated polypropylene, polychlorotrifluoroethylene and polytetrafluoroethylene;

Polymers of α,β-unsaturated acids and their derivatives

Polyacrylic acid esters, polymethacrylic acid esters, polyacrylamides and polyacrylonitriles;

Polymers of unsaturated alcohols and unsaturated amines or their acyl derivatives or acetals Polyvinyl alcohols, polyvinyl acetate, polyvinyl stearate, polyvinyl benzoate, polyvinyl maleate, polyvinyl butyral, polyallyl phthalate or polyallyl melamine, and copolymers of such monomers with other vinyl compounds (e.g. ethylene-vinyl acetate copolymer);

Polyalkylene oxides and polyphenylene oxides

Polyoxymethylene, oxymethylene-ethylene oxide copolymer, polyoxyethylene, polypropylene oxide, polyisobutylene oxide and polyphenylene oxide;

Modified celluloses

Cellulose acetate, cellulose acetate butyrate, cellulose acetate propionate, cellulose propionate, nitrocellulose and ethyl cellulose;

Polyamides and copolyamides

Polyamides and copolyamides derived from diamines and aliphatic acids or aromatic dicarboxylic acids and/or from aminocarboxylic acids or corresponding lactams (e.g. Nylon 6, Nylon 6/6, Nylon 6/10, Nylon 11 and Nylon 12);

Polyesters

Polyesters derived from dicarboxylic acids and dialcobols and/or from oxyacids or corresponding lactones (e.g. polyethylene terephthalate, polybutylene terephthalate, polycyclohexane-1,4-dimethylene terephthalate);

Polycarbonates, polyester carbonates, polyether imides, polyether ketones, polyether sulfones, polyphenylene sulfides, polysulfones and silicone resins Polyurethanes and polyureas Cross-linked polymers Cross-linked polymers consisting of a moiety derived from aldehydes and another moiety derived from phenol, urea or melamine (e.g. phenol formaldehyde resins, urea-formaldehyde resins, melamine-formaldehyde resins and diaryl phthalate resins);

Epoxy polymers

Homopolymers and copolymers of epoxy compounds (e.g. polyethylene oxide); and polymers of bisglycidyl ether compounds;

Alkyd resins

Glycerol-phthalic acid resins and mixtures thereof with melamine-formaldehyde resins;

Unsaturated polyester resins

Unsaturated polyester resins derived from copolyesters of saturated and unsaturated dicarboxylic acids and polyhydric alcohols and prepared using vinyl compounds as cross-linking agents; and unsaturated polyester resins modified by chlorination for enhanced flame retardancy.

The quantity of stabilizer of the present invention necessary to achieve the desired stabilization effect will vary depending on a number of factors which will be clear to those skilled in the art. However, typical factors which need to be taken into account include the type of polymer to be stabilized, its properties and its intended use, and especially whether other additives are to be used. In general, though, we prefer to use from about 0.01 to about 5% by weight of the stabilizer of the present invention based on the weight of the polymer.

The preferred amount used, as stated above, will vary depending on the kind of polymer. For example, for olefin, diene and styrene polymers, suitable amounts of stabilizer are from about 0.01 to about 2.0% by weight, preferably from about 0.05 to about 2.0% by weight; for vinyl chloride and vinylidene chloride polymers suitable amounts are from about 0.01 to about 5.0% by weight, preferably from about 0.05 to about 2.0% by weight; and for polyurethane and polyamide polymers, suitable amounts are from about 0.01 to about 5.0% by weight, preferably from about 0.05 to about 2.0% by weight.

It will be appreciated that two or more stabilizers of the present invention may be used in combination or with any other additives, as desired.

Various kinds of additives customarily used in the field of polymer technology can suitably be added separately or together with the stabilizers of the present invention. Suitable such additives include, for example:

Phenol antioxidants 2,6-di-t-Butyl-p-cresol; stearyl-β-(4-hydroxy-3,5-di-t-butylphenyl) propionate; distearyl (4-hydroxy-3-methyl-5-t-butylbenzyl) malonate; 2,2'-methylenebis-(4-methyl-6-t-butylphenol); 4,4-methylenebis (2,6-di-t-butylphenol); 2,2'-methylenebis[6-(1-methylcyclohexyl)-p-cresol]; bis[3,3-bis (4-hydroxy-3-t-butylphenyl) butyric acid] glycol ester; 4,4'-butylidenebis (6-t-butyl-m-cresol); 1,1,3-tris(2-methyl-4-hydroxy-5-t-butyl-phenyl)butane; 1,3,5 - tris(3,5-di-t-butyl-4- hydroxy benzyl)-2,4,6-trimethylbenzene; 3,9-bis [1,1-dimethyl-2-(3,5-di-t-butyl-4-hydroxyphenyl) ethyl]-2,4,8,10-tetraoxaspiro [5,5]undecane; pentaerythrityl tetrakis-[3-(3,5-di-t-butyl-4-hydroxyphenyl) propionate]; 1,3,5-tris (3,5-di-t-butyl-4-hydroxybenzyl) isocyanurate; 1,3,5-tris [(3,5-di-t-butyl-4-hydroxyphenyl) propionyl-oxyethyl]isocyanurate; and bis [3-(3,5-di-t-butyl-4 -hydroxyphenyl)propionyl]oxamide.

Thioester Stabilizers

Dilauryl thiodipropionate, dimyristyl thiodipropionate, distearyl thiodipropionate, and pentaerythrityl tetrakis (dodecylthiopropionate).

Phosphite stabilizers

Tris(2,4-di-t-butylphenyl) phosphite; triphenyl phosphite; tris(nonylphenyl) phosphite; distearyl pentaerythritol diphosphite; 4,4-butylidenebis-( 3-methyl-6-t-butylphenyl-di-tridecyl) phosphite; bis(2,4-di-t-butylphenyl) pentaerythritol diphosphite; and tetrakis(2,4-di-t-butylphenyl) 4,4-biphenylene phosphonite.

Hindered amine photostabilizers

4-Benzoyloxy-2,2,6,6-tetramethylpiperidine;
4-stearoyloxy-2,2,6,6-tetramethylpiperidine;
4-methacryloyloxy-2,2,6,6-tetramethylpiperidine;
4-methacryloyloxy-1,2,2,6,6-pentamethylpiperidine;
bis(2,2,6,6-tetramethyl-4-piperidinyl) sebacate;
bis(1,2,2,6,6-pentamethyl-4-piperidinyl) sebacate;
bis(2,2,6,6-tetramethyl-1-octoxy-4-piperidinyl) sebacate;
2-methyl-2-(2,2,6,6-tetramethyl-4-piperidinyl)imino-N-(2,2,6,6-tetramethyl-4-piperidinyl)propionarnide;
2-methyl-2-(1,2,2,6,6-pentamethyl-4-piperidinyl)imino-N-(1,2,2,6,6-pentamethyl-4-piperidinyl)propionamide;
1-acryloyl-4-benzyloxy-2,2,6,6-tetramethylpiperidine;
bis(1,2,2,6,6-pentamethyl-4-piperidinyl)-2-butyl-2-(3,5-di-t-butyl-4-hydroxybenzyl)butyl malonate;
8-acetyl-3-dodecyl-7,7,9,9-tetramethyl-1,3,8-triazaspiro[4,5]decane-2,4-dione;
tetrakis(2,2,6,6-tetramethyl-4-piperidinyl)-1,2,3,4-butanetetracarboxylate;
tetrakis(1,2,2,6,6-pentamethyl-4-piperidinyl)-1,2,3,4-butanetetracarboxylate;
tridecyl-tris(2,2,6,6-tetramethyl-4-piperidyl)-1,2,3,4-butanetetracarboxylate;
tridecyl.tris(1,2,2,6,6-pentamethyl-4-piperidyl)-1,2,3,4-butanetatracarboxylate;
4-{3-(3,5-di-t-butyl-4-hydroxyphenyl)propionyloxy}-1-[2-{3-(3,5-di-t-butyl-4-hydroxyphenyl)propionyloxy-}ethyl]2,2,6,6-tetramethylpiperidine;
ditridecyl.bis(2,2,6,6-tetramethyl-4-piperidinyl)-1,2,3,4-butanetetracarboxylate;
ditridecyl -bis(1,2,2,6,6-pentamethyl-4-piperidinyl)-1,2,3,4-butanetetracarboxylate;
3,9 -bis [1,1-dimethyl-2-{tris (2,2,6,6-tetramethyl-4-piperidinyloxycarbonyl)butylcarbonyloxy-}ethyl]-2,4,8,10- tetraoxaspiro[5,5]undecane;
3,9-bis [1,1-dimethyl-2-(tris{1,2,2,6,6-pentamethyl -4-piperidyloxycarbonyl)butylcarbonyloxy}ethyl]-2,4,8,10-tetraoxaspiro [5,5]undecane;
dimethyl succinate 4 - hydroxy-1-(2-hydroxyethyl)-2,2,6,6-tetramethylpiperidine polycondensation product;
poly [ethylene{(2,2,6,6-tetramethyl-4-piperidinyl)-imino}hexamethylene{(2,2,6,6-tetramethyl-4-piperidinyl)-imino}];
poly [{6-(1,1,3,3-tetramethylbutyl)amino-1,3,5-triazine-2,4-diyl}{(2,2,6,6-tetramethyl-4-piperidyl)-imino}-hexamethylene {(2,2,6,6-tetramethyl-4-piperidinyl)-imino}];
poly [{6-(cyclohexylamino)-1,3,5-triazine -2,4-diyl}-{(2,2,6,6,-tetramethyl-4-piperidinyl)imino}hexa-methylene{(2,2,6,6-tetramethyl-4-piperidinyl) imino}];
poly [{6-(morpholino)-1,3,5-triazine-2,4-diyl}-{(2,2,6,6-tetramethyl-4-piperidinyl) imino}hexa-methylene- {(2,2,6,6-tetramethyl-4-piperidinyl) imino}];
1,6,11-tris [{4,6 -bis (N-butyl-N-(2,2,6,6-tetramethyl-4-piperidyl)amino)-1,3,5-triazin-2-yl}amino]azaundecane;
1,6,11-tris [{4,6-bis (N-butyl-N-(1,2,2,6,6-pentamethyl-4-piperidyl) amino) -1,3,5-triazin-2-yl}amino] azaundecane;
1,5,8,12-tetrakis[4,6-bis{N-butyl-N-(1,2,2,6,6-pentamethyl-4-piperidinyl) amino)-1,3,5-triazin-2-yl]-1,5,8,12-tetraazadodecane; and
polymethylpropyl-3 -oxy [4-(2,2,6,6-tetramethyl)-piperidinyl]siloxane. Particularly preferred are bis (2,2,6,6-tetramethyl-4-piperidinyl) sebacate; bis (1,2,2,6,6-pentamethyl -4-piperidinyl) sebacate; tetrakis (2,2,6,6-tetramethyl-4-piperidinyl) 1,2,3,4-butanetetracarboxylate; tetrakis (1,2,2,6,6-pentamethyl-4-piperidinyl) 1,2,3,4-butanetetracarboxylate; dimethyl succinate 4 -hydroxy- 1-(2-hydroxyethyl)-2,2,6,6-tetramethyl-piperidine polycondensation product; poly [{6-(1,1,3,3-tetramethyl-butyl)amino-1,3,5 -triazine -2,4-diyl}{(2,2,6,6-tetramethyl 4-piperidinyl)imino}-hexamethylene {(2,2,6,6-tetramethyl-4-piperidyl)

imino}]; poly [{6-morpholino-1,3,5-triazine-2,4-diyl}{ (2,2,6,6-tetramethyl-4-piperidyl)imino}-hexamethylene{ (2,2,6,6-tetramethyl-4-piperidyl) imino}]; and 1,5,8,12-tetrakis{4,6-bis-(N-1,2,2,6,6,-pentamethyl-4-piperidyl)-butylamino}-1,3,5-triazin-2-yl]-1,5,8,12-tetraazadodecane.

Ultraviolet absorbers 2,4-Dihydroxybenzophenone, 2-hydroxy-4-methoxybenzophenone; 2-hydroxy-4-methoxybenzophenone-5-sulfonic acid; 2-hydroxy-4-octoxybenzophenone; 2-hydroxy-4-dodecyloxybenzophenone; 2-hydroxy-4-benzyloxybenzophenone; bis(5-benzoyl-4-hydroxy-2-methoxyphenyl)methane; 2,2'-dihydroxy-4-methoxybenzophenone; 2,2'-dihydroxy-4,4'-dimethoxybenzophenone; 2,2',4,4'-tetrahydroxybenzophenone; 2,hydroxy-4-methoxy-2'-carboxybenzophenone; 2-(2'-hydroxy-5'-methylphenyl) benzotriazole; 2-[2'-hydroxy-3',5'-bis(α,α-dimethylbenzyl)-phenyl]benzotriazole; 2-(2'-hydroxy-3',5'-di-t-butyl-phenyl) benzotriazole; 2-(2'-hydroxy-3'-t-butyl-5'-methylphenyl)-5-chlorobenzotriazole; 2-(2'-hydroxy-3',5'-di-t-butyl-phenyl)-5-chlorobenzotriazole; 2-(2'-hydroxy-3',5'-di-t-amylphenyl)-benzotriazole; 2-(2'-hydroxy-5'-t-octylphenyl)-benzotriazole; 2,2'-methylene-bis[4-(1,1,3,3-tetramethylbutyl)-6-(2N-benzotriazol-2-yl)phenol]; a condensation product of methyl-3-[3-t-butyl-5-(2H-benzotriazol-2-yl)-4-hydroxyphenyl] propionate and polyethylene glycol; and 2-(2-hydroxyphenyl)benzotriazole copolymer.

Hydroxybenzoate photostabilizers 2,4-di-t-butylphenyl 3,5-di-t-butyl-4-hydroxybenzoate, 2,6-di-t-butylphenyl 3,5-di-t-butyl-4-hydroxybenzoate, and hexadecyl 3,5-di-t-butyl-4-hydroxybenzoate.

Nickel-containing stabilizers

Nickel monoethyl-3,5-di-t-butyl-4-hydroxybenzyl-phosphonate; butylamine-nickel-2,2'-thiobis-(4-t-octylphenolate) complex; nickel dibutyl-dithiocarbamate; and nickel 3,5-di-t-butyl-4-hydroxybenzoate.

Metal salts of higher fatty acids

Calcium, magnesium, barium, zinc, cadmium, lead or nickel stearate, and calcium, magnesium, cadmium, barium or zinc laurate.

The various additives of the types listed above may, of course, be used singly or in combinations of two or more, as appropiate to the intended purpose.

The stabilizers of the present invention may also be used in combination with such other agents as heavy metal deactivators, nucleating agents, organic tin compounds, plasticizers, epoxy compounds, pigments, paints, fluorescent brighteners, fillers, boosters, foaming agents, antistatic agents, mildew-proofing or bactericidal agents, lubricants and processing aids.

Polymers incorporating the stabilizers of the present invention can be used as desired, such as in the form of films, sheets, fibers, tapes, compression molding materials, injection molding materials, coating compositions, sealing materials or adhesives.

Embodiments of the present invention will now be described more fully by way of the accompanying Examples and Reference Examples, which are non-limiting on the scope of the invention. In the accompanying Examples and Reference Examples, "parts" and "%", where used, mean parts by weight and % by weight, respectively, unless otherwise specified.

Starting materials used in the Examples are adducts of alkylene oxides with various alcohols, which may be described as alkylene glycol monoethers or as O-alkylated alkylene glycols. These are commercially available or can be prepared by known methods, e.g. as described at pages 141–142 in "Synthesis and Applications of Surface Active Agents" by Ryohei Oda and Kazuhiro Teramura 13th edition (1972) published Maki Publishing Co. Ltd., Japan. As previously explained, the commercially available adducts may be mixtures of several individual compounds with varying numbers of ethylene oxide and/or propylene oxide units, so that the number of units indicated in the name of the compound may therefore represent the average number in such a mixture.

EXAMPLE 1

2-{2-[2-(2-ethylhexyloxy) ethoxy]ethoxy}propyl 3-(3,5-di-t-butyl-4-hydroxyphenyl)propionate A mixture consisting of 50 ml of toluene, 12.51 g of 3-(3,5-di-t-butyl-4-hydroxyphenyl)propionic acid, 8.29 g of an adduct of O-(2-ethylhexyl)diethylene glycol with 1 mol of propylene oxide, and 0.16 g of p-toluenesulfonic acid was heated under reflux for 6 hours with stirring, then the water which formed was distilled off. The reaction mixture was left to cool and then washed with 5% aqueous sodium bicarbonate solution and water. The toluene was stripped off under reduced pressure, giving 13.6 g of the title compound as a pale yellow oil with $n_D^{20}$ 1.4885.

EXAMPLE 2

Condensation product of O-(2-ethylhexyl) octaethylene glycol and methyl-3-(3,5-di-t-butyl-4-hydroxyphenyl)-propionate A mixture of 370 ml of xylene, 92.1 g of methyl 3-(3,5-di-t-butyl-4-hydroxyphenyl)propionate, 145.6 g of an adduct of 2-ethylhexyl alcohol with ethylene oxide (1:8 molar ratio) and 0.5 g of tetraisopropyl orthotitanate was heated under reflux for 3.5 hours with stirring, then the mixture of toluene and methanol which formed was distilled off. The reaction mixture was left to cool and then washed with 30 ml of water. The xylene was stripped off under the reduced pressure, giving 215.5 g of the title compound as a pale yellow oil with $n_D^{20}$ 1.4845.

EXAMPLE 3

Condensation product of O-dodecyldiethylene glycol and 3-(3,5-di-t-butyl-4-hydroxyphenyl) propionic acid The title compound was prepared from an adduct of dodecyl alcohol with ethylene oxide (1:2 molar ratio), by a procedure analogous to that of Example 1, as a pale yellow oil with $n_D^{20}$ 1.4877.

EXAMPLE 4

Condensation product of O-dodecyldipropylene glycol and 3-(3,5-di-t-butyl-4-hydroxyphenyl) propionic acid The title compound was prepared from an adduct of dodecyl alcohol with propylene oxide (1:2 molar ratio), by a procedure analogous to that of Example 1, as an oil with $n_D^{20}$ 1.4831.

EXAMPLE 5

O-dodecyloctaethylene glycol 3-(3,5-di-t-butyl-4-hydroxyphenyl)propionate

A mixture consisting of 40 ml of toluene, 1.08 g of methyl 3-(3,5-di-t-butyl-4-hydroxyphenyl)propionate, 2.0 g of O-dodecyloctaethylene glycol (specific gravity 0.889 20/4° C., available from Wako Pure Chemical Industries, Ltd.) and 0.1 g of tetraisopropyl orthotitanate was heated under reflux with stirring for 7 hours, then the mixture of toluene and methanol which formed was distilled off. The reaction mixture was left to cool and then filtered. Water was added to the flitrate, and the reaction product was extracted three times with 20 ml of ethyl acetate. The extract was dried over anhydrous magnesium sulfate and concentrated. The residue was purified by column chromatography (eluted with ethyl acetate/n-hexane=⅓) giving 2.15 g of the title compound as an oil with $n_D^{20}$ 1.4823.

Elemental Analysis: Calculated for $C_{45}H_{82}O_{11}$: C: 67.63%; H: 10.34%; Found: C: 67.35%; H: 10.36%.

EXAMPLE 6

Condensation product of O-hexadecylethylene glycol and 3-(3,5-di-t-butyl-4-hydroxyphenyl) propionic acid The title compound was prepared from an adduct of hexadecyl alcohol with ethylene oxide (1:1 molar ratio), by a procedure analogous to that of Example 1, as an oil with $n_D^{20}$ 1.4868.

EXAMPLE 7

Condensation product of O-hexadecyldiethylene glycol and methyl-3-(3,5-di-t-butyl-4-hydroxyphenyl)propionate A mixture consisting of 150 ml of toluene, 53.5 g of methyl 3-(3,5-di-t-butyl-4-hydroxyphenyl)propionate, 60.0 g of an adduct of hexadecyl alcohol with ethylene oxide (1:2 molar ratio, $n_D^{45}$ 1.4428) and 0.9 g of tetraisopropyl orthotitanate was heated under reflux for 10 hours with stirring, then the mixture of toluene and methanol which formed was evaporated off. Water (8.3 ml) was added to the reaction mixture, the resulting mixture was stirred under reflux for 1 hour, and then the water and toluene were evaporated off. The reaction mixture was filtered, and the filtrate was concentrated under reduced pressure giving 101.6 g of the title compound as a slightly yellowish oil with $n_D^{20}$ 1.4867.

EXAMPLE 8

Condensation product of O-hexadecyltriethylene glycol and methyl-3-(3,5-di-t-butyl-4-hydroxyphenyl)propionate The title compound was prepared from an adduct of hexadecyl alcohol with ethylene oxide (1:3 molar ratio), by a procedure analogous to that of Example 7, as an oil with $n_D^{20}$ 1.4850.

EXAMPLE 9

Condensation product of O-hexadecyldipropylene glycol and 3-(3,5-di-t-butyl-4-hydroxyphenyl) propionic acid The title compound was prepared from an adduct of hexadecyl alcohol with propylene oxide (1:2 molar ratio), by a procedure analogous to that of Example 2, as a slightly yellowish oil with $n_D^{20}$ 1.4800.

EXAMPLE 10

Condensation product of O-Hexadecyldiethylene glycol and and methyl-3-(3-t-butyl-4-hydoxy-5-methylphenyl)propionate A mixture consisting of 30 ml of toluene, 7.5 g of methyl 3-(3-t-butyl-4-hydoxy-5-methylphenyl)propionate, 10 g of an adduct of hexadecyl alcohol with ethylene oxide (1:2 molar ratio, $n_D^{45}$ 1.4428) and 0.02 g of sodium methoxide was heated under reflux with stirring for 6 hours, then the mixture of toluene and methanol which formed was distilled off. The reaction mixture was left to cool, then neutralised with 5% aqueous sulfuric acid, washed twice with water, dried over anhydrous sodium sulfate and concentrated, giving 15.7 g of the title compound as an oil with $n_D^{20}$ 1.4887.

EXAMPLE 11

Condensation product of O-octadecyldiethylene glycol and 3-(3,5-di-t-butyl-4-hydroxyphenyl) propionic acid The title compound was prepared from an adduct of octadecyl alcohol with ethylene oxide (1:2 molar ratio), by a procedure analogous to that of Example 1, as an oil with $n_D^{20}$ 1.4855.

EXAMPLE 12

Condensation product of O-octadecyldipropylene glycol and methyl-3-(3,5-di-t-butyl-4-hydroxyphenyl)propionate The title compound was prepared from an adduct of octadecyl alcohol with propylene oxide (1:2 molar ratio), by a procedure analogous to that of Example 10, as a pale yellow oil with $n_D^{20}$ 1.4805.

EXAMPLE 13

Condensation product of O-octadecyltripropylene glycol and 3-(3,5-di-t-butyl-4-hydroxyphenyl) propionic acid The title compound was prepared from an adduct of octadecyl alcohol with propylene oxide (1:3 molar ratio), by a procedure analogous to that of Example 1, as a pale yellow oil with $n_D^{20}$ 1.4783.

EXAMPLE 14

Heat Stability Test

Unstabilized polypropylene powder having a melt flow rate of about 4.0 was kneaded with 0.1% of antioxidant (specified in Table 2) in a mixer (Laboplasto™ mill, manufactured by Toyo Seiki Seisakusho) at 200° C. for 10 minutes, to homogeneity. The resulting homogeneous preparation was immediately rolled into a sheet of about 2–3 mm thickness, using a water-cooled hydraulic press.

A portion of this sheet was cut out and was pressed at 240° C. for 4 minutes in the press to obtain a 0.5 mm thick sheet. Test strips cut from this 0.5 mm sheet, measuring 10×100 mm, were placed in an oven at 130° C. and the number of days recorded until oxidative degradation (whitening) occurred. The results are shown in Table 2.

In Table 2, the compounds of the invention are identified by reference to the numbers in the compound list of Table 1, and also by reference to the above Examples illustrating their preparation. The Comparative Compounds 1 and 2 are the compounds prepared in Reference Examples 1 and 2 below, respectively, and form part of the prior art disclosed in GB Patent 1,376,482.

TABLE 2

| Test Compound | | Heat resistance |
|---|---|---|
| Example | Compound List | at 130° C. (days) |
| Example 1 | No. 11 | 11 |
| Example 2 | No. 8 | 13 |
| Example 3 | No. 21 | 16 |
| Example 4 | No. 24 | 12 |
| Example 5 | No. 23 | 10 |
| Example 6 | No. 35 | 18 |
| Example 7 | No. 36 | 26 |
| Example 8 | No. 37 | 22 |
| Example 9 | No. 42 | 25 |
| Example 10 | No. 28 | 21 |
| Example 11 | No. 53 | 29 |
| Example 12 | No. 58 | 26 |
| Example 13 | No. 59 | 16 |
| Comparative Compound 1 | | 5 |
| Comparative Compound 2 | | 4 |

Comparative Example 1

2-Methoxyethyl 3-(3,5-di-t-butyl-4-hydroxyphenyl)propionate

The title compound was prepared from 90 g of toluene, 102.4 g of methyl 3-(3,5-di-t-butyl-4-hydroxyphenyl)propionate, 18.2 g of ethylene glycol monomethyl ether and 0.35 g of sodium methoxide, by a procedure analogous to that of Example 10. Yield 42.2 g. Melting point 62°–64° C.

Reference Example 2

2-Methoxypropyl 3-(3,5-di-t-butyl-4-hydroxyphenyl)propionate

The title compound was prepared from methyl 3-(3,5-di-t-butyl-4-hydroxyphenyl)propionate and propylene glycol monomethyl ether, by a procedure analogous to that of Reference Example 10. White powder with mellting point 73°–74° C.

We claim:

1. A compound of formula

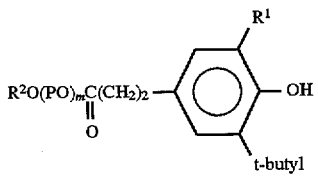

wherein:
$R^1$ represents an alkyl group having from 1 to 6 carbon atoms;
$R^2$ represents a straight chain or branched alkyl group having from 8 to 24 carbon atoms;
PO represents a propyleneoxy group; and
m is an integer from 1 to 5.

2. The compound of claim 1, wherein:
$R^1$ represents an alkyl group having from 1 to 4 carbon atoms; and
$R^2$ represents an alkyl group having from 8 to 18 carbon atoms.

3. The compound of claim 1, wherein:
$R^1$ represents a methyl or t-butyl group; and
$R^2$ represents an alkyl group having from 12 to 18 carbon atoms.

4. The compound of claim 1, wherein:
$R^1$ represents a t-butyl group;
$R^2$ represents an alkyl group having from 16 to 18 carbon atoms; and
M is from 1 to 3.

5. A polymer composition stabilized against oxidation, comprising at least one polymeric material and an effective amount of a compound of the formula

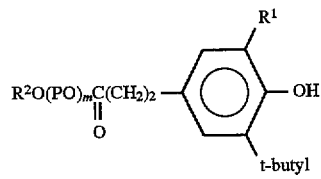

wherein:
$R^1$ represents an alkyl group having from 1 to 6 carbon atoms;
$R^2$ represents a straight chain or branched alkyl group having from 8 to 24 carbon atoms;
PO represents a propyleneoxy group; and
m is an integer from 1 to 5.

6. The composition of claim 5, comprising from 0.01% to by weight of said compound based on the weight of said polymeric material.

7. The composition of claim 6, wherein:
$R^1$ represents an alkyl group having from 1 to 4 carbon atoms; and
$R^2$ represents an alkyl group having from 8 to 18 carbon atoms.

8. The composition of claim 6, wherein:
$R^1$ represents a methyl or t-butyl group; and
$R^2$ represents an alkyl group having from 12 to 18 carbon atoms.

9. The composition of claim 6, wherein:
$R^1$ represents a t-butyl group;
$R^2$ represents an alkyl group having from 16 to 18 carbon atoms; and
M is from 1 to 3.

10. The compound of claim 3, wherein $R^1$ is t-butyl.
11. The compound of claim 10, wherein m is 1.
12. The compound of claim 10, wherein m is 2.
13. The compound of claim 10, wherein m is 3.
14. The compound of claim 10, wherein m is 4.
15. The compound of claim 10, wherein m is 5.
16. The compound of claim 10, wherein $R^2$ is dodecyl.
17. The compound of claim 10, wherein $R^2$ is tridecyl.
18. The compound of claim 10, wherein $R^2$ is hexadecyl.
19. The compound of claim 4, wherein $R^2$ is hexadecyl and m is 3.
20. The composition of claim 8, wherein $R^1$ is t-butyl.
21. The composition of claim 20, wherein m is 1.
22. The compound of claim 20, wherein m is 2.
23. The composition of claim 20, wherein m is 3.
24. The composition of claim 20, wherein m is 4.
25. The composition of claim 20, wherein m is 5.
26. The composition of claim 20, wherein $R^2$ is dodecyl.
27. The composition of claim 20, wherein $R^2$ is tridecyl.

28. The composition of claim 20, wherein $R^2$ is hexadecyl.

29. The composition of claim 8, wherein $R^2$ is hexadecyl and m is 3.

30. A compound of formula (I):

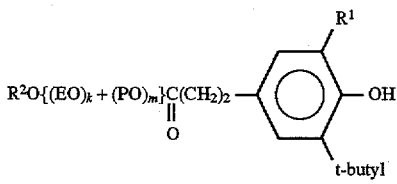 (I)

wherein:

$R^1$ represents an alkyl group having from 1 to 6 carbon atoms;

$R^2$ represents an alkyl group having from 8 to 24 carbon atoms;

EO represents an ethyleneoxy group;

PO represents a propyleneoxy group;

k is 0 or an integer from 1 to 10; and m is an integer from 1 to 4;

provided that the total of (k+m) is greater than 1 and not greater than 10.

31. The compound of claim 30, wherein:

$R^1$ represents an alkyl group having from 1 to 4 carbon atoms;

$R^2$ represents an alkyl group having from 8 to 18 carbon atoms; and the total of (k+m) is from 1 to 8.

32. The compound of claim 30, wherein:

$R^1$ represents a methyl or t-butyl group;

$R^2$ represents an alkyl group having from 12 to 18 carbon atoms; and the total of (k+m) is from 1 to 6.

33. The compound of claim 30, wherein:

$R^1$ represents a t-butyl group;

$R^2$ represents an alkyl group having from 16 to 18 carbon atoms; and the total of (k+m) is from 1 to 3.

34. A polymer composition stabilized against oxidation, comprising at least one polymeric material and an effective amount of a compound of formula (I):

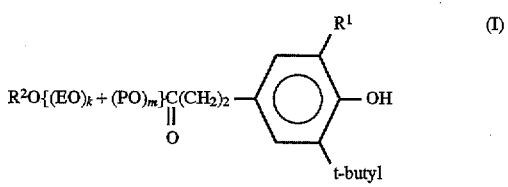 (I)

wherein:

$R^1$ represents an alkyl group having from 1 to 6 carbon atoms;

$R^2$ represents an alkyl group having from 8 to 24 carbon atoms;

EO represents an ethyleneoxy group;

PO represents a propyleneoxy group;

k is 0 or an integer from 1 to 10; and m is an integer from 1 to 4;

provided that the total of (k+m) is greater than 1 and not greater than 10.

35. The composition of claim 34, comprising a compound of said formula (I) wherein:

$R^1$ represents an alkyl group having from 1 to 4 carbon atoms;

$R^2$ represents an alkyl group having from 8 to 18 carbon atoms; and the total of (k+m) is from 1 to 8.

36. The composition of claim 34, comprising a compound of said formula (I) wherein:

$R^1$ represents a methyl or t-butyl group;

$R^2$ represents an alkyl group having from 12 to 18 carbon atoms; and the total of (k+m) is from 1 to 6.

37. The composition of claim 34, comprising a compound of said formula (I) wherein:

$R^1$ represents a t-butyl group;

$R^2$ represents an alkyl group having from 16 to 18 carbon atoms; and the total of (k+m) is from 1 to 3.

38. The composition of claim 34, comprising from 0.01% to 5% by weight of said compound of formula (I) based on the weight of said polymeric material.

39. The compound of claim 1, wherein m is 3, $R^2$ is a $C_{16}$ alkyl group and $R^1$ is t-butyl.

40. The composition of claim 5, wherein m is 3, $R^2$ is a $C_{16}$ alkyl group and $R^1$ is t-butyl.

* * * * *

UNITED STATES PATENT AND TRADEMARK OFFICE
CERTIFICATE OF CORRECTION

PATENT NO. : 5,739,377
DATED : April 14, 1998
INVENTOR(S) : OHSAWA et al

It is certified that error appears in the above-identified patent and that said Letters Patent is hereby corrected as shown below:

Column 6, line 56: delete "ms" and insert --is--.

Column 15, line 32: delete "Reference" and insert --Comparative--.

Column 16, line 28 (Claim 6): after "to" insert --5%--.

Colum 17, line 3 (Claim 29): delete "8" and insert --9--;
line 4: rewrite "is3" as --is 3--.

Signed and Sealed this

Fifteenth Day of February, 2000

Attest:

Q. TODD DICKINSON

*Attesting Officer*      *Commissioner of Patents and Trademarks*